(12) United States Patent
Gearheart et al.

(10) Patent No.: US 12,070,260 B2
(45) Date of Patent: *Aug. 27, 2024

(54) SYSTEM AND METHOD FOR INDICATING RETURN ELECTRODE CONTACT

(71) Applicant: COVIDIEN LP, Mansfield, MA (US)

(72) Inventors: John R. Gearheart, Boston, MA (US); David Hubelbank, Newmarket, NH (US)

(73) Assignee: Covidien LP, Mansfield, MA (US)

( * ) Notice: Subject to any disclaimer, the term of this patent is extended or adjusted under 35 U.S.C. 154(b) by 311 days.

This patent is subject to a terminal disclaimer.

(21) Appl. No.: 17/533,696

(22) Filed: Nov. 23, 2021

(65) Prior Publication Data

US 2022/0079653 A1    Mar. 17, 2022

Related U.S. Application Data

(63) Continuation of application No. 16/414,578, filed on May 16, 2019, now Pat. No. 11,185,362.

(51) Int. Cl.
*A61B 18/12* (2006.01)
*A61B 18/14* (2006.01)
*A61B 18/00* (2006.01)

(52) U.S. Cl.
CPC .......... *A61B 18/1233* (2013.01); *A61B 18/14* (2013.01); *A61B 2018/0072* (2013.01); *A61B 2018/00755* (2013.01); *A61B 2018/00767* (2013.01); *A61B 2018/1253* (2013.01)

(58) Field of Classification Search
CPC . A61B 18/1233; A61B 18/14; A61B 18/1402; A61B 18/16; A61B 2018/00702; A61B 2018/0072; A61B 2018/00755; A61B 2018/00767; A61B 2018/00875; A61B 2018/1253; A61B 90/30; A61B 2090/306
See application file for complete search history.

(56) References Cited

U.S. PATENT DOCUMENTS

| | | |
|---|---|---|
| 4,494,541 A | 1/1985 | Archibald |
| 5,560,372 A | 10/1996 | Cory |
| 5,817,091 A | 10/1998 | Nardella et al. |
| 6,676,660 B2 | 1/2004 | Wampler et al. |
| 7,736,359 B2 | 6/2010 | McPherson |
| 7,865,236 B2 | 1/2011 | Cory et al. |
| 8,080,007 B2 | 12/2011 | Dunning et al. |
| 8,118,807 B2 | 2/2012 | Thiagalingam et al. |
| 8,187,263 B2 | 5/2012 | Behnke et al. |
| 11,185,362 B2 | 11/2021 | Gearheart et al. |
| 2002/0107517 A1 | 8/2002 | Witt et al. |
| 2002/0111624 A1 | 8/2002 | Witt et al. |
| 2006/0247683 A1 | 11/2006 | Danek et al. |
| 2008/0195089 A1 | 8/2008 | Thiagalingam |

(Continued)

*Primary Examiner* — Michael F Peffley
(74) *Attorney, Agent, or Firm* — Carter, DeLuca & Farrell LLP

(57) ABSTRACT

An electrosurgical system monitors and visually indicates a degree of contact between a return electrode and a patient's skin. The system includes an electrosurgical generator and a return pad. The return pad includes a return electrode, a lighting element, and a cable electrically and mechanically coupling the return electrode to the generator. The lighting element is configured to emit light based on the degree of contact between the return electrode and the patient.

19 Claims, 3 Drawing Sheets

(56) References Cited

U.S. PATENT DOCUMENTS

| | | | |
|---|---|---|---|
| 2015/0157392 A1* | 6/2015 | Rivera | A61B 18/1492 |
| | | | 606/48 |
| 2016/0045247 A1 | 2/2016 | Heim et al. | |
| 2016/0338759 A1 | 11/2016 | Schnitzler et al. | |
| 2017/0056127 A1* | 3/2017 | Dunning | A61B 18/1445 |

* cited by examiner

SYSTEM AND METHOD FOR INDICATING RETURN ELECTRODE CONTACT

CROSS-REFERENCE TO RELATED APPLICATIONS

This application is a continuation of U.S. patent application Ser. No. 16/414,578, filed on May 16, 2019, now U.S. Pat. No. 11,185,362.

INTRODUCTION

The present disclosure relates generally to electrosurgical systems and methods. More particularly, the present disclosure is directed to electrosurgical systems and methods for return electrode monitoring, including monitoring the quality of contact between return electrode pads and the patient during electrosurgical procedures.

BACKGROUND

Energy-based tissue treatment is well-known in the art. Various types of energy (such as electrical, ultrasonic, microwave, cryogenic, heat, laser, and/or the like) are applied to tissue to achieve a desired result. Electrosurgery involves application of high radio frequency electrical current to a surgical site to cut, ablate, coagulate, seal or otherwise treat tissue. Energy-based surgical devices typically include an isolation boundary between the patient and the energy source.

In monopolar electrosurgery, the active electrode is typically part of the surgical instrument held by the surgeon and applied to the tissue to be treated. One or more patient return electrodes are placed remotely from the active electrode to carry the current back to the generator and disperse current applied by the active electrode. The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

Early types of return electrodes were formed as large metal plates covered with conductive jelly. Later, adhesive electrodes were developed with a single metal foil covered with conductive jelly or conductive adhesive. However, one challenge that arises from employing adhesive electrodes is that, if a portion of an adhesive electrode peels from the patient, the contact area of the electrode with the patient decreases, thereby increasing the current density at the adhered portion and, in turn, decreasing the effectiveness of the treatment.

SUMMARY

In accordance with aspects of the disclosure, a patient return pad is provided. The patient return pad includes a return electrode, a return lead, a translucent sheathing, and a lighting element. The return electrode is configured to be coupled to a patient and to receive electrosurgical energy from an active electrode. The return lead has a first end portion coupled to the return electrode and a second end portion configured to electrically couple the return electrode to an electrosurgical energy source. The translucent sheathing is disposed on the return lead. The lighting element is disposed at least partially within the translucent sheathing and is configured to illuminate to emit light through the translucent sheathing based on a measured impedance to indicate a degree of contact between the return electrode and a patient's tissue.

In an aspect of the present disclosure, the light emitted by the lighting element may be configured to be varied based on the measured impedance of the return electrode.

In another aspect of the present disclosure, the lighting element may be a plurality of lighting elements disposed along a length of the return lead.

In an aspect of the present disclosure, the lighting element may be disposed on the first end portion of the return lead adjacent the return electrode.

In yet another aspect of the present disclosure, the lighting element may be configured to emit a predetermined amount of light that is proportional to an amount of contact between the return electrode and the patient's tissue.

In a further aspect of the present disclosure, the lighting element may include at least one of an LED or a lighting fiber.

In an aspect of the present disclosure, the translucent sheathing may define a longitudinally-extending pathway.

In a further aspect of the present disclosure, the return electrode may be a split foil electrode.

In accordance with aspects of the disclosure, an electrosurgical system is presented. The electrosurgical system includes an electrosurgical energy source and a patient return pad. The electrosurgical energy source is configured to generate electrosurgical energy and includes a monitoring circuit. The patient return pad includes a return electrode, a return lead, a translucent sheathing, and a lighting element. The return electrode is configured to be coupled to a patient and to receive the electrosurgical energy from an active electrode. The monitoring circuit is configured to be electrically coupled to the return electrode for determining an impedance thereof. The return lead has a first end portion coupled to the return electrode and a second end portion configured to be electrically and mechanically coupled to the electrosurgical energy source. The translucent sheathing disposed over the return lead. The lighting source is disposed at least partially within the translucent sheathing and is configured to illuminate to emit light through the translucent sheathing based on the determined impedance. The electrosurgical energy source is configured to vary a characteristic of the light emitted through the translucent sheathing based on the determined impedance of the return electrode.

In yet another aspect of the present disclosure, the electrosurgical energy source may be configured to vary the characteristic of the light emitted through the translucent sheathing in response to a change in the determined impedance.

In a further aspect of the present disclosure, the system may further include a monopolar electrosurgical instrument configured for electrical connection to the electrosurgical energy source and for delivering the electrosurgical energy.

In yet a further aspect of the present disclosure, the electrosurgical energy source may include an indicator light configured to turn on or off based on the determined impedance.

In yet another aspect of the present disclosure, the translucent sheathing may include fiber optics for passing the light from the indicator light to an end portion of the translucent sheathing.

In a further aspect of the present disclosure, the monitoring circuit may be configured to turn the indicator light on or off based on the determined impedance.

In yet a further aspect of the present disclosure, the characteristic of the light is at least one of brightness, intensity, or illuminance.

In yet another aspect of the present disclosure, the lighting element may include a plurality of lighting elements disposed along a length of the return lead.

In a further aspect of the present disclosure, the lighting element may be disposed on the first end portion of the return lead adjacent the return electrode.

In an aspect of the present disclosure, the lighting element may be configured to emit a predetermined amount of light that is proportional to an amount of contact between the return electrode and the patient's tissue.

In another aspect of the present disclosure, the lighting element may include at least one of an LED or a lighting fiber.

In a further aspect of the present disclosure, a method for lighting a return electrode is presented. The method includes generating, by an electrosurgical energy source, electrosurgical energy, delivering the electrosurgical energy to tissue from a monopolar electrosurgical instrument that is coupled to the electrosurgical energy source via a cable, and emitting light through a translucent sheathing of the cable, and varying a characteristic of the light emitted through the translucent sheathing based on the determined impedance of the return electrode.

Further details and aspects of exemplary embodiments of the disclosure are described in more detail below with reference to the appended figures. Any of the above aspects and embodiments of the disclosure may be combined without departing from the scope of the disclosure.

BRIEF DESCRIPTION OF THE DRAWINGS

The above and other aspects, features, and advantages of the present disclosure will become more apparent in light of the following detailed description when taken in conjunction with the accompanying drawings, in which.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A system and method for return electrode monitoring are provided. The system includes a split foil electrode configured to be coupled to a patient for measuring electrical signals, a monitoring circuit of an electrosurgical energy source electrically coupled to the split foil electrode, and a cable electrically and mechanically coupling the electrode to the electrosurgical energy source. The monitoring circuit is configured to measure an impedance of the split foil electrode. The cable has a translucent sheathing and a lighting element disposed at least partially within the translucent sheathing. The lighting element is configured to illuminate based on the measured impedance to indicate to a clinician a degree of adherence of the return electrode to a patient's tissue.

Figure 1:
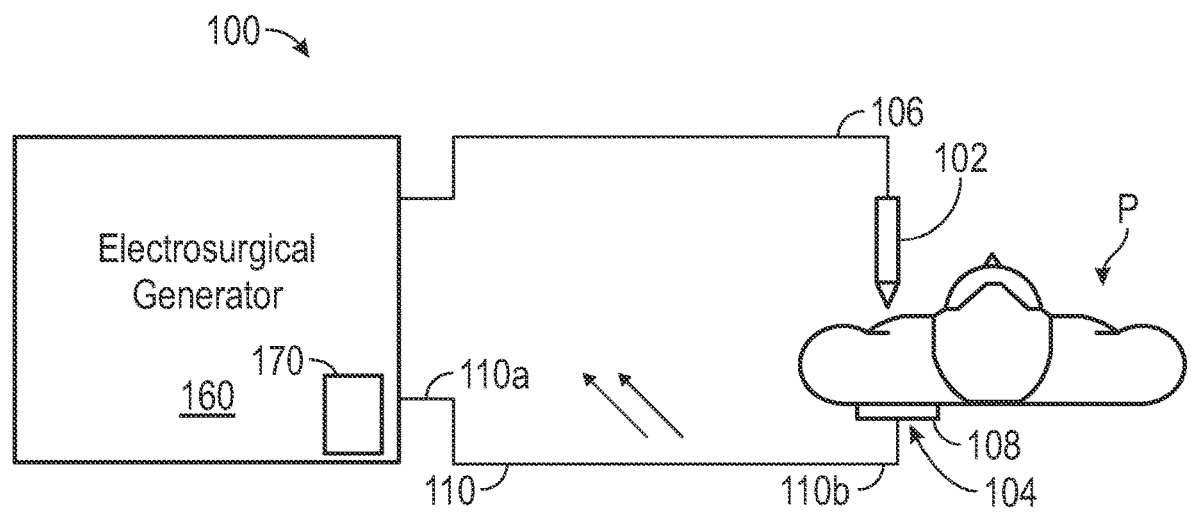
FIG. 1 is a schematic illustration of a system for indicating return electrode contact with a patient according to the present disclosure.

FIG. 1 illustrates an electrosurgical system 100 including an electrosurgical energy source, such as, for example, an electrosurgical generator 160, an electrosurgical instrument 102 coupled to the generator 160, and a patient return pad 104 coupled to the generator 160 via a return cable 110. The electrosurgical instrument 102 has one or more active electrodes (not explicitly shown) for treating tissue of a patient P. The instrument 102 may be a monopolar instrument including one or more active electrodes (such as, for example, an electrosurgical cutting probe, ablation electrode(s), and/or the like). Electrosurgical RF energy is supplied to the instrument 102 by the generator 160 via an active electrosurgical cable 106, which is connected to an active output terminal, allowing the instrument 102 to coagulate, ablate and/or otherwise treat tissue.

Although the generator 160 is described herein as delivering RF energy, this is by example only and should not be construed as limiting. The generator 160 in various embodiments may additionally or alternatively deliver any suitable type of energy, such as ultrasonic energy, microwave energy, energy of other portions on the electromagnetic spectrum, and/or the like. The energy is returned to the generator 160 through the patient return pad 104, as will be described. The generator 160 includes input controls (for example, buttons, activators, switches, touch screen, etc.) for controlling the generator 160. In addition, the generator 160 may include one or more display screens for providing the user with variety of output information (for example, intensity settings, treatment complete indicators, etc.). The controls allow the user to adjust power of the RF energy, waveform, and other parameters to achieve the desired waveform suitable for a particular task (for example, coagulating, cauterizing, intensity setting, etc.). The instrument 102 may also include a plurality of input controls that may be redundant with certain input controls of the generator 160. Placing the input controls at the instrument 102 allows for easier and faster modification of RF energy parameters during the surgical procedure without requiring interaction with the generator 160.

Figure 2:
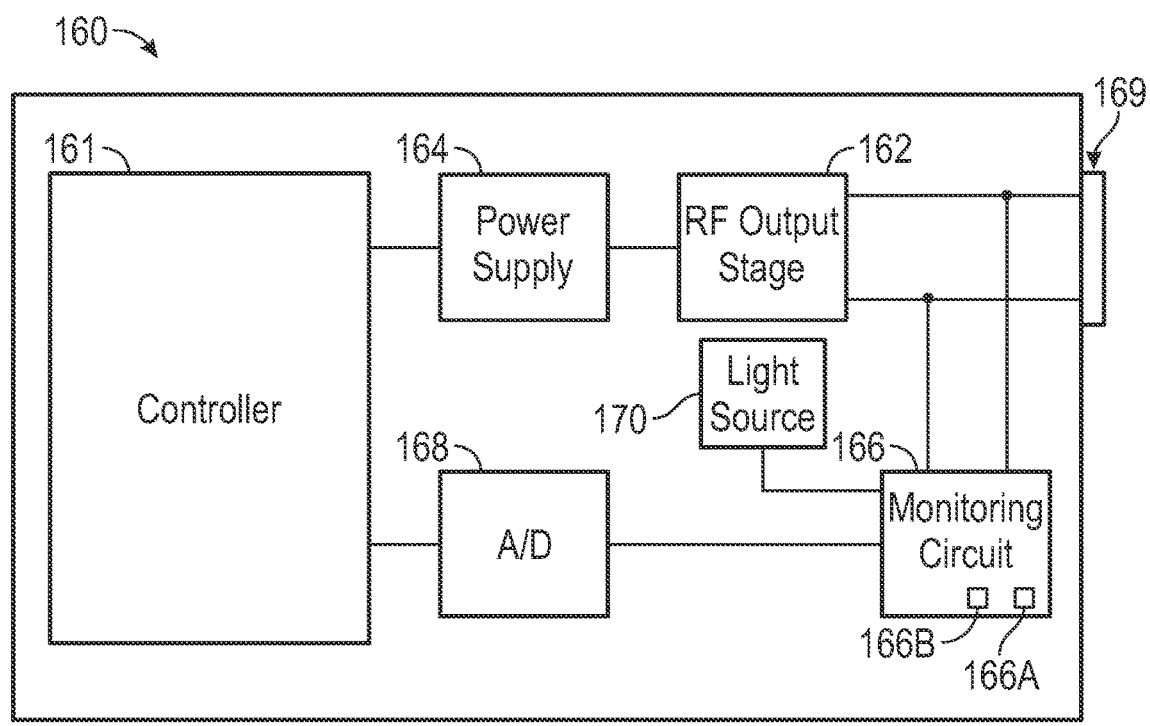
FIG. 2 is a block diagram of a generator of the system of FIG. 1.

Referring now to FIG. 2, there is shown a block diagram of exemplary components of the electrosurgical generator 160 in accordance with aspects of the disclosure. In the illustrated embodiment, the generator 160 includes a controller 161, a power supply 164, a radio-frequency (RF) energy output stage 162, a monitoring circuit 166, and one or more plugs 169 that accommodate various types of electrosurgical instruments. The generator 160 can include a user interface (not shown), which permits a user to select various parameters for the generator 160, such as mode of operation and power setting. In various embodiments, the power setting can be specified by a user to be between zero and a power limit, such as, for example, five watts, thirty watts, seventy watts, or ninety-five watts.

The electrosurgical generator 160 may be any suitable type of generator and may include a plurality of connectors to accommodate various types of electrosurgical instruments (e.g., monopolar, bipolar, and/or the like). The electrosurgical generator 160 may also be configured to operate in a variety of modes, such as ablation, cutting, coagulation, cutting/coagulation blend, sealing, or any combination thereof. The electrosurgical generator 160 may include a switching mechanism (e.g., relays) to switch the supply of RF energy among the one or more plugs 169 to which various electrosurgical instruments may be connected. For example, when an electrosurgical instrument, e.g., instrument 102, is connected to the electrosurgical generator 160, the switching mechanism switches the supply of RF energy to the plug 169 to which instrument 102 is connected. In embodiments, the electrosurgical generator 160 may be configured to provide RF energy to a plurality of instruments simultaneously.

The monitoring circuit 166 of the generator may include a plurality of sensors, e.g., an RF current sensor, an RF voltage sensor, and/or the like. Various components of the generator 160, e.g., the RF output stage 162 and the RF current and voltage sensors 166A, 166B of the monitoring circuit 166, may be disposed on a printed circuit board (PCB). The RF current sensor 166A of the monitoring circuit 166 may be coupled to the active electrode and provides measurements of the RF current supplied by the RF output stage 162. In embodiments, the RF current sensor 166A of the monitoring circuit 166 may be coupled to the return electrode. The RF voltage sensor 166B of the monitoring circuit 166 is coupled to the active terminal and a return terminal and provides measurements of the RF voltage supplied by the RF output stage 162. In embodiments, the RF current and voltage sensors 166A, 166B of the monitoring circuit 166 may be coupled to the active and return cables 106, 110 (FIG. 1), which interconnect the active and return terminals to the RF output stage 162, respectively.

The RF current and voltage sensors 166A, 166B of the monitoring circuit 166 sense and provide the sensed RF voltage and current signals, respectively, to the controller 161 of the generator 160, which then may adjust output of the power supply and/or the RF output stage 162 in response to the sensed RF voltage and current signals. The sensed voltage and current from the monitoring circuit 166 are fed to an analog-to-digital converter (ADC) 168 of the generator 160. The ADC 168 samples the sensed voltage and current to obtain digital samples of the voltage and current of the RF output stage 162. The digital samples are processed by the controller 161 and used to generate a control signal to control the DC/AC inverter of the RF output stage 162 and the preamplifier. The ADC 168 communicates the digital samples to the controller 161 for further processing. Examples of the processing include deriving the impedance of a return electrode 108 (FIG. 1) from the sensed voltage and current.

The monitoring circuit 166 may include a hand switch closure detection sensor (not explicitly shown) configured to detect closure of a hand switch of the surgical instrument 102, a return electrode monitoring sensor (not explicitly shown) configured to detect an impedance associated with the return electrode 108 (e.g., for embodiments where the surgical instrument 102 is a monopolar electrosurgical instrument), a temperature sensor (not explicitly shown), a mechanical force sensor (not explicitly shown), and/or any other suitable type of sensor.

The generator 160 may include a light source 170 (FIG. 1) configured to indicate the detected impedance associated with the return electrode 108 (e.g., a neutral electrode indication light emitted from the electrosurgical generator 160). In various embodiments, the light source 170 may include, but is not limited to an LED, an incandescent bulb, or a XENON source. The light source 170 may be powered by the power supply 164 or an external battery.

Figure 3:
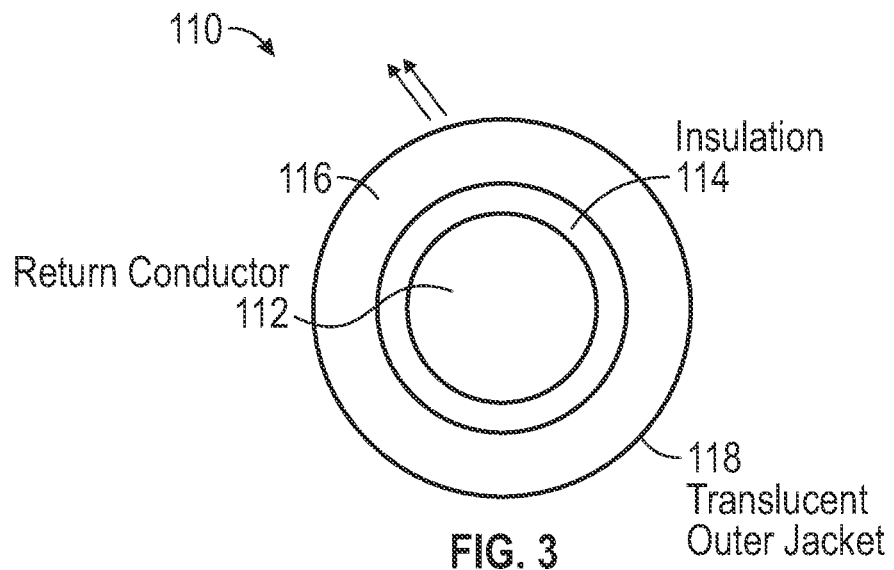
FIG. 3 is a transverse cross sectional view of a cable of the system of FIG. 1 illustrating a return lead and a translucent sheathing disposed thereabout.
Figure 4:
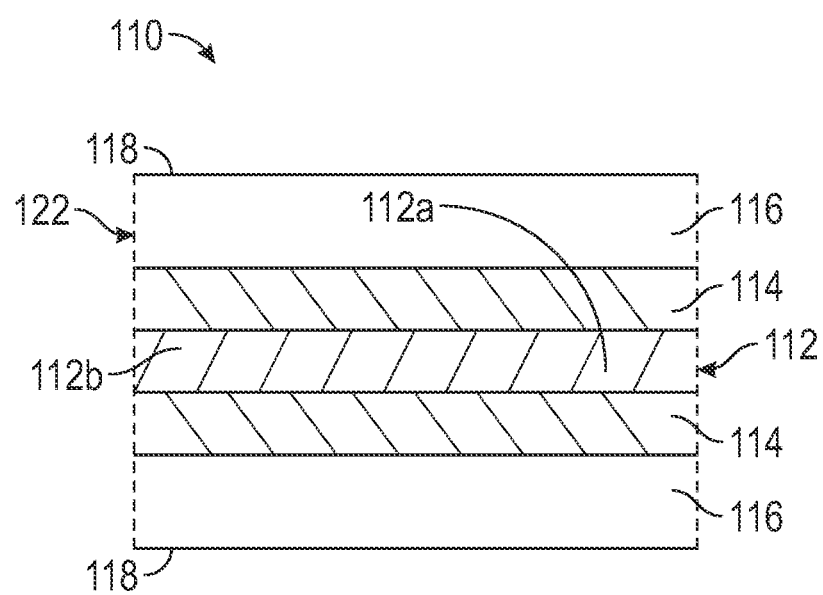
FIG. 4 is a longitudinal cross sectional view of the cable of FIG. 3.

With reference to FIGS. 1, 3, and 4, the patient return pad 104 of the electrosurgical system 100 generally includes a return electrode 108 and a return cable 110. The return electrode 108 is configured to be positioned in contact with the patient P and return the electrosurgical energy to the generator 160 by way of the return cable 110. The electrosurgical system 100 may include a plurality of return electrodes 108 that are arranged to minimize the chances of tissue damage by maximizing the overall contact area with the patient P.

FIGS. 3 and 4 are cross sections of the return cable 110 of the patient return pad 104. The return cable 110 is configured for illumination based on the impedance determined by the monitoring circuit 166 of the generator 160. The return cable 110 has a first end portion 110a coupled to the return electrode 108 and a second end portion 110b configured to be detachably coupled to an electrosurgical energy source, such as the generator 160 (FIG. 2).

The return cable 110 includes a return conductor 112 (e.g., a return lead), an insulator 114 disposed about the return conductor 112, a lighting fiber 116 disposed about the insulator 114, and a translucent conductor sheathing 118 disposed about the lighting fiber 116. The return conductor 112 is coupled to the RF output stage 162 (FIG. 2) of the generator 160 and to the monitoring circuit 166 for return electrode monitoring. The return conductor 112 is configured to electrically couple the return electrode 108 to the generator 160. The return conductor 112 may be any suitable conductive material for an electrode lead (e.g., copper). The conductor 112 has a first end portion 112a coupled to the return electrode 108 and a second end portion 112b configured to be detachably coupled to an electrosurgical energy source, such as the generator 160 (FIG. 2).

The insulator 114 of the return cable 110 may be any suitable insulating material (e.g., silicone, PVC, TFE, Alcryn, Cellular Polyethylene, Ethylene Propylenediene Monomer Rubber, etc.). The lighting fiber 116 extends from the generator 160 to the return electrode 108 and is disposed within the translucent conductor sheathing 118. The lighting fiber 116 is configured to facilitate the passage of light therealong. In embodiments, instead of a lighting fiber 116, the return cable 110 may define a longitudinally-extending lumen between the insulator 114 and the translucent conductor sheathing 118 for guiding light from the light source 170 of the generator 160 (FIG. 2) to the second end portion 110b of the return cable 110. The first end portion 110a of the return cable 110 may be coupled to a location of the generator 160 adjacent the light source 170, such that light emitted from the light source 170 may enter the return cable 110 via the first end portion 110a thereof.

Light is transmitted from the light source 170, through the lighting fiber 116, and emitted out the translucent conductor sheathing 118. The monitoring circuit 166 may control the light source 170 of the generator 160 to illuminate based on the impedance of the return electrode 108 detected by the monitoring circuit 166. Characteristics of the light emitted by the light source 170, such as brightness, intensity, illuminance, etc., may be predetermined and/or varied in proportion to the impedance and/or conductivity of the return electrode 108 (e.g., light brightness increases as impedance of the return electrode increases to provide a conspicuous indication of poor contact between the return electrode 108 and the patient P). In embodiments, only the second end portion 110b of the return cable 110 may have the translucent conductor sheathing 118, whereas the remaining portion of the return cable 110 has an opaque sheathing. As such, when the light source 170 is activated, the light travels through the opaque sheathing to the second end portion 110b of the return cable 110, whereupon the light transmits out of the distal second end portion 110b of the return cable 110.

During an electrosurgical procedure, the return electrode 108 (FIG. 1) of the return pad 104 is placed on tissue of a patient P (e.g., skin) and the monopolar electrode of the surgical instrument 102 is activated to treat tissue. During treatment, the electrosurgical energy passes from the generator 160, through the electrosurgical instrument 102 and into a patient P to treat the tissue. The electrosurgical energy then travels from the tissue back to the electrosurgical generator 160 via the return pad 104. Prior to and/or during the procedure, the monitoring circuit 166 of the generator 160 determines impedance of the return electrode 108. In particular, the monitoring circuit 166 senses and provides the sensed RF voltage and current signals of the electrosurgical energy passing through the return electrode to the controller 161 of generator 160, which may adjust output of the power supply and/or the RF output stage 162 in response to the sensed RF voltage and current signals. The sensed voltage and current signals are processed by the controller 161 and an impedance value of the return electrode 108 is determined. Light is transmitted from the light source 170, through the lighting fiber 116, and emitted out the translucent conductor sheathing 118 so that a surgeon is able to see the illuminated return cable 110 in their peripheral vision without having to move their head to see the indicator light, e.g. light source 170, on the generator 160. In this way, the illuminated return cable 110 provides the surgeon with a conspicuous visual indication of contact quality between the return electrode 108 and the patient based on the determined impedance of the return electrode 108.

In various embodiments, the impedance may be determined based on the sensed RF voltage and sensed RF current measurements. In embodiments, the impedance may be determined by conducting a sense pulse from the electrosurgical instrument through the tissue and measuring the change in the pulse shape across the load, e.g. the tissue.

In one non-limiting example, the electrosurgical system 100 may detect a conductivity of the return electrode 108 as an impedance of about 100 ohms and may have a predetermined luminance of about 1200 lumens. In another non-limiting example, the electrosurgical system 100 may detect a conductivity of the return electrode 108 as an impedance of about 1000 ohms and may have a predetermined luminance of about 10 lumens.

Figure 5:
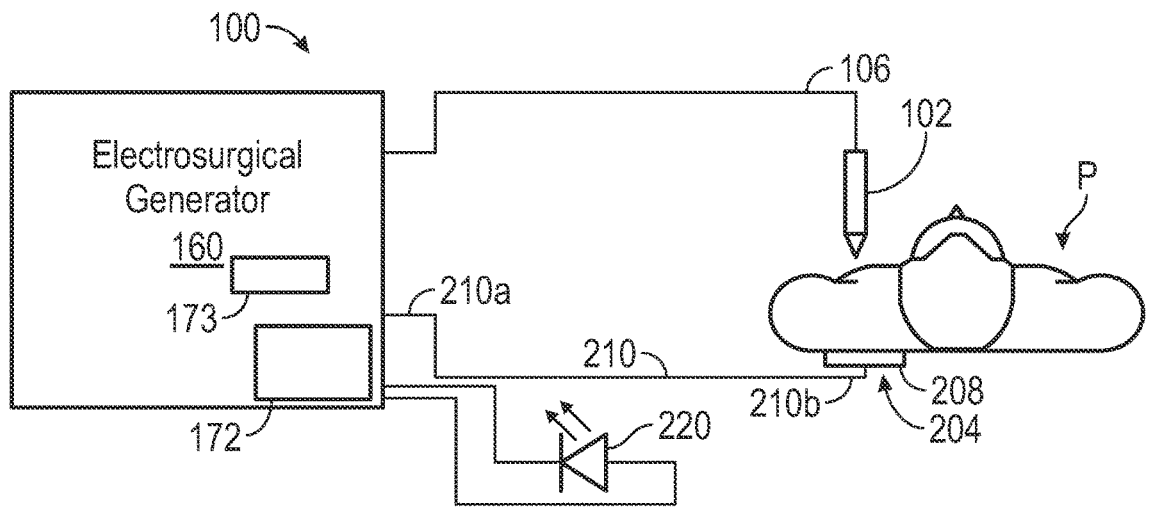
FIG. 5 is a schematic illustration of another embodiment of a system for indicating return electrode contact with a patient according to the present disclosure.

FIG. 5 is a schematic illustration of an electrosurgical system 200 according to another embodiment of the present disclosure. The electrosurgical system 200 is similar to the system 100 and will only be described in the detail necessary to elucidate differences between the two.

The system 200 includes a patient return pad 204 including a return electrode 208 and a return cable 210 coupling the return electrode 208 to an electrosurgical energy source, such as, for example, the generator 160. The patient return pad 204 differs from the patient return pad 104 of FIGS. 1-4 by having a lighting element 220 disposed within the return cable 210. Characteristics of the light emitted from lighting element 220, such as brightness, intensity, illuminance, etc., may be predetermined and/or varied by the controller 161 in proportion to the impedance and/or conductivity of the return electrode 208. The lighting element 220 may be powered by the generator 160 or an external power source (e.g., a battery). The generator 160 may include a control unit 172 operatively coupled to the lighting element 220. The control unit 172 is configured to control the brightness of the lighting element 220 to provide a visual indication of the impedance of the return electrode 208.

Figure 6:
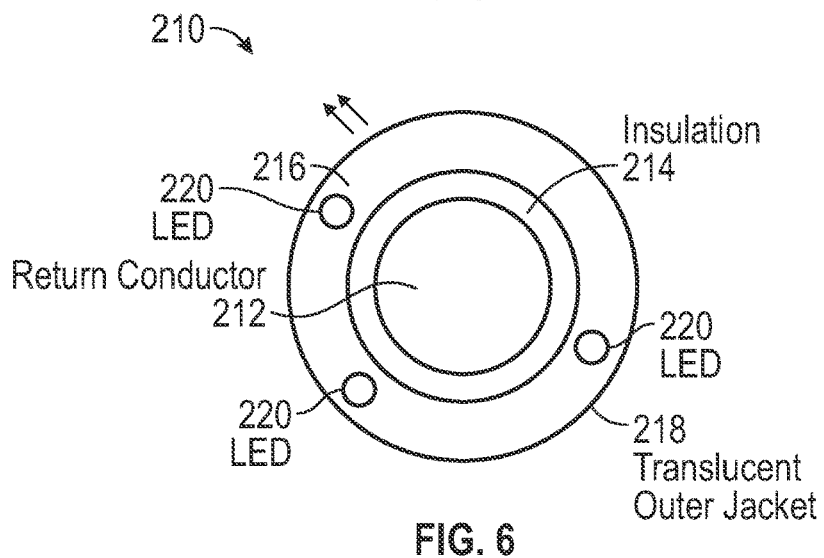
FIG. 6 is a transverse cross sectional view of a cable of the system of FIG. 5.
Figure 7:
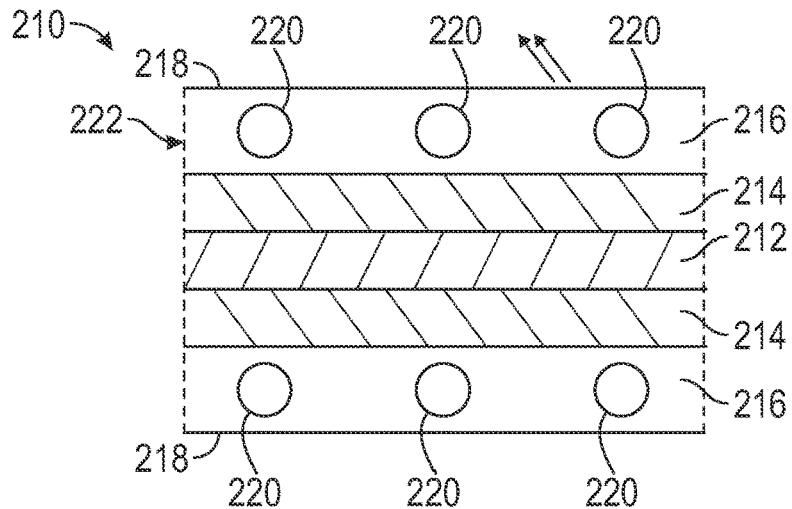
FIG. 7 is a longitudinal cross sectional view of the cable of FIG. 5.

FIGS. 6 and 7 are cross sections of the return cable 210. The cable 210 is configured for illumination based on the detected impedance of the return electrode 208. The cable 210 has a first end portion 210a configured to be electrically and mechanically coupled to the generator 160, and a second end portion 210b having the return electrode 208 coupled thereto. The cable 210 includes a return conductor 212, an insulator 214, a lighting fiber 216, a translucent conductor sheathing 218, and the lighting element 220. The return conductor 212 is configured to electrically couple the return electrode 208 to the generator 160. The return conductor 212 may be any suitable conductive material for an electrode lead (e.g., copper). The conductor 212 has a first end portion coupled to the return electrode 208 and a second end portion configured to be detachably coupled to an electrosurgical energy source, such as the generator 160 (FIG. 2).

The translucent conductor sheathing 218 defines a longitudinally-extending passageway 222 through which the lighting fiber 216 extends. The lighting element 220 (e.g., one or more LEDs, bulbs, etc.) may be disposed within the lighting fiber 216. In various embodiments, translucent or transparent materials other than lighting fiber 216 may be used. In embodiments, the LEDs may be in a series or parallel configuration. In other aspects, the lighting element 220 may be disposed in air or a vacuum.

The lighting element 220 may include multicolor LEDs configured to light predetermined colors based on the detected impedance of the return electrode 208. For example, the LEDs may illuminate green at lower impedance values, denoting good contact between the patient P and the return electrode 208, yellow at a middle impedance value, and red at very high impedance values, denoting poor contact between the patient P and the return electrode 208.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but are not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (for example, stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A patient return pad, comprising:
    a return electrode configured to be coupled to a patient and to receive electrosurgical energy from an active electrode;
    a return lead having a first end portion coupled to the return electrode and a second end portion configured to electrically couple the return electrode to an electrosurgical energy source;
    a translucent sheathing disposed over at least a portion of the return lead; and
    a lighting element disposed at least partially within the translucent sheathing.

2. The patient return pad according to claim 1, wherein the lighting element is configured to illuminate and emit light through the translucent sheathing based on a measured impedance.

3. The patient return pad according to claim 2, wherein illumination of the lighting element is configured to indicate a degree of contact between the return electrode and the patient.

4. The patient return pad according to claim 2, wherein light emitted by the lighting element is configured to be varied based on the measured impedance of the return electrode.

5. The patient return pad according to claim 1, wherein the lighting element includes a plurality of lighting elements disposed along a length of the return lead.

6. The patient return pad according to claim 1, wherein the lighting element is located at the first end portion of the return lead adjacent the return electrode.

7. The patient return pad according to claim 1, wherein the lighting element is configured to emit a predetermined amount of light that is proportional to an amount of contact between the return electrode and the patient.

8. The patient return pad according to claim 1, wherein the lighting element includes at least one of an LED or a lighting fiber.

9. The patient return pad according to claim 1, wherein the translucent sheathing defines a longitudinally-extending pathway.

10. The patient return pad according to claim 1, wherein the return electrode is a split foil electrode.

11. An electrosurgical system, comprising:
    an electrosurgical energy source configured to generate electrosurgical energy, the electrosurgical energy source including a monitoring circuit; and
    a patient return pad including:
        a return electrode configured to be coupled to a patient and to a monitoring circuit associated with the electrosurgical energy source for determining an impedance of the return electrode;
        a return lead having a first end portion coupled to the return electrode and a second end portion configured to be coupled to the electrosurgical energy source; and
        a translucent sheathing disposed about the return lead.

12. The electrosurgical system according to claim 11, wherein the return pad further includes a lighting element disposed at least partially within the translucent sheathing.

13. The electrosurgical system according to claim 12, wherein the lighting element is configured to illuminate and emit light through the translucent sheathing based on the determined impedance.

14. The electrosurgical system according to claim 13, wherein the electrosurgical energy source has an indicator light configured to turn on or off based on the determined impedance.

15. The electrosurgical system according to claim 14, wherein the patient return pad includes fiber optics for passing the light from the indicator light to an end portion of the translucent sheathing.

16. The electrosurgical system according to claim 14, wherein the monitoring circuit is configured to turn the indicator light on or off based on the determined impedance.

17. The electrosurgical system according to claim 13, wherein the electrosurgical energy source is configured to vary a characteristic of the light emitted through the translucent sheathing based on the determined impedance of the return electrode.

18. The electrosurgical system according to claim 12, wherein the electrosurgical energy source is configured to vary the characteristic of the light emitted through the translucent sheathing in response to a change in the determined impedance.

19. The electrosurgical system according to claim 11, further comprising a monopolar electrosurgical instrument configured for electrical connection to the electrosurgical energy source and for delivering the electrosurgical energy.

* * * * *